United States Patent [19]

Fisher

[11] Patent Number: 5,345,947
[45] Date of Patent: Sep. 13, 1994

[54] WRIST AND ANKLE SECURED RESTRAINING DEVICE

[76] Inventor: David P. Fisher, 1116 Crescent, Wichita Falls, Tex. 76305

[21] Appl. No.: 96,268

[22] Filed: Jul. 26, 1993

[51] Int. Cl.⁵ .......................... A61F 5/37; E05B 75/00
[52] U.S. Cl. ........................................ 128/878; 70/16
[58] Field of Search ............... 128/876, 882, 869, 878; 428/100; 70/14, 15, 16, 18; 297/466; 119/96, 109, 126

[56] References Cited

U.S. PATENT DOCUMENTS

| | | |
|---|---|---|
| 879,534 | 2/1908 | Fraser . |
| 1,536,551 | 5/1925 | Young ................................. 119/128 |
| 2,295,806 | 9/1942 | Peterson ............................. 128/134 |
| 2,324,183 | 7/1943 | Wilson ................................. 70/16 |
| 2,645,922 | 7/1953 | Martin ................................. 70/16 |
| 3,369,842 | 2/1968 | Adams et al. ....................... 297/389 |
| 3,426,559 | 2/1969 | Schubach et al. .................... 70/16 |
| 4,422,455 | 12/1983 | Olsen ................................. 128/134 |
| 4,526,165 | 7/1985 | Mielnik, Jr. et al. ............... 128/133 |
| 4,728,553 | 3/1988 | Daniels ............................... 428/100 |
| 4,854,138 | 8/1989 | Charland ............................. 128/878 |
| 4,949,679 | 8/1990 | Wolfer ................................. 128/878 |
| 5,005,527 | 4/1991 | Hatfield ............................... 119/109 |

Primary Examiner—Robert A. Hafer
Assistant Examiner—Michael O'Neill
Attorney, Agent, or Firm—Dougherty, Hessin, Beavers & Gilbert

[57] ABSTRACT

A restraining device for use in securing a hand-cuffed prisoner consisting of a control strap gripped through a releasable cam buckle that is resiliently secured to the handcuffs. A selected amount of control strap is looped around the prisoner's ankles and led through the cam buckle to expose the control end which may be pulled to shorten the control strap connection between ankles and handcuffs, or the cam buckle can be actuated to release the control strap thereby to allow greater prisoner freedom and movement.

8 Claims, 1 Drawing Sheet

WRIST AND ANKLE SECURED RESTRAINING DEVICE

BACKGROUND OF THE INVENTION

1. Field of the Invention

The invention relates generally to devices for restraining prisoners and, more particularly, but not by way of limitation, it relates to an improved type of restraining device for use in combination with handcuffs to restrain the prisoner by bonding the wrists and ankles together to whatever degree necessary to disable the prisoner.

2. Description of the Prior Art

The prior art includes numerous types of physical restraining devices which have been previously developed for use in law enforcement, military and the like undertakings. One early form of restraining mechanism utilizing strap elements is illustrated by U.S. Pat No. 2,295,806. In this case, the device is a surgical restraining device, which includes a first belt for cinching the knees of the patient together and a second waist belt for enveloping the patient's wrists, thereafter to be strapped securely within the waist belt. This device includes additional belts for connection between the knee strap and the waist belt which tend to immobilize the patient still further. Another restraining belt which is the subject of U.S. Pat. No. 4,422,455 consists of a device having a cuff part used in combination with a strap which includes a quick release attachment loop for affixture to the patient's bedside rail or the like. Generally this device will be duplicated, one on each arm or leg of a patient, with strap anchoring via the loop on each side of the patient's bed.

A recently developed form of prisoner restraining device is taught in U.S. Pat. No. 4,728,553 which provides a releasable hook attachment and leather strap for connecting between a prisoner's knee strap and a hook-eye fixture on the floorboard of an auto or the like. This device functions to retain a prisoner seated in a patrol car or the like as the VELCRO ®-attached knee strap maintains limited motion while his wrists are cuffed behind his back. Other forms of restraint apparatus encountered during searching relative to the present disclosure include various forms of strap or belt locking apparatus and numerous types of seat belt-type restraints, as well as the aforementioned prisoner restraint wherein a prisoner's limbs are strapped in locked relationship to the floorboard of a vehicle.

SUMMARY OF THE INVENTION

The present invention relates to an improved type of prisoner restraining device which is used in combination with handcuffs or similar wrist binding. The restraining device is an elongated strap having a brass ring on one end for forming a loop that is placed around the prisoner's ankles. The elongated strap is then led through a quick-release cam type slide fastener which is connected to a short length of strap having a snap hook thereon. The free end of the elongated strap can then be used for adjustment through the slide fastener to lengthen or shorten the length between the ankle loop and the snap hook which is then connected to the prisoner's handcuffs. Thus, a tug on the free end of the strap can shorten the effective length between ankle loop and snap hook thereby increasingly restraining the prisoner.

Therefore, it is an object of the present invention to provide a quick-release restraining strap for use in controlling a handcuffed prisoner.

It is also an object of the present invention to provide a restraining device that can be quickly released and removed from a prisoner once he has been delivered to a place of detention.

It is also an object of the present invention to provide a prisoner restraining device that can be secure yet either comfortable or severely restrictive depending upon the exigencies of the situation.

Finally, it is an object of the present invention to provide versatile, positive restraint for prisoners of either large or small body size as it serves to keep a prisoner under control at all times, either while standing or sitting in a squad car.

Other objects and advantages of the invention will be evident from the following detailed description when read in conjunction with the accompanying drawings which illustrate the invention.

DETAILED DESCRIPTION OF THE INVENTION

Figure 1:
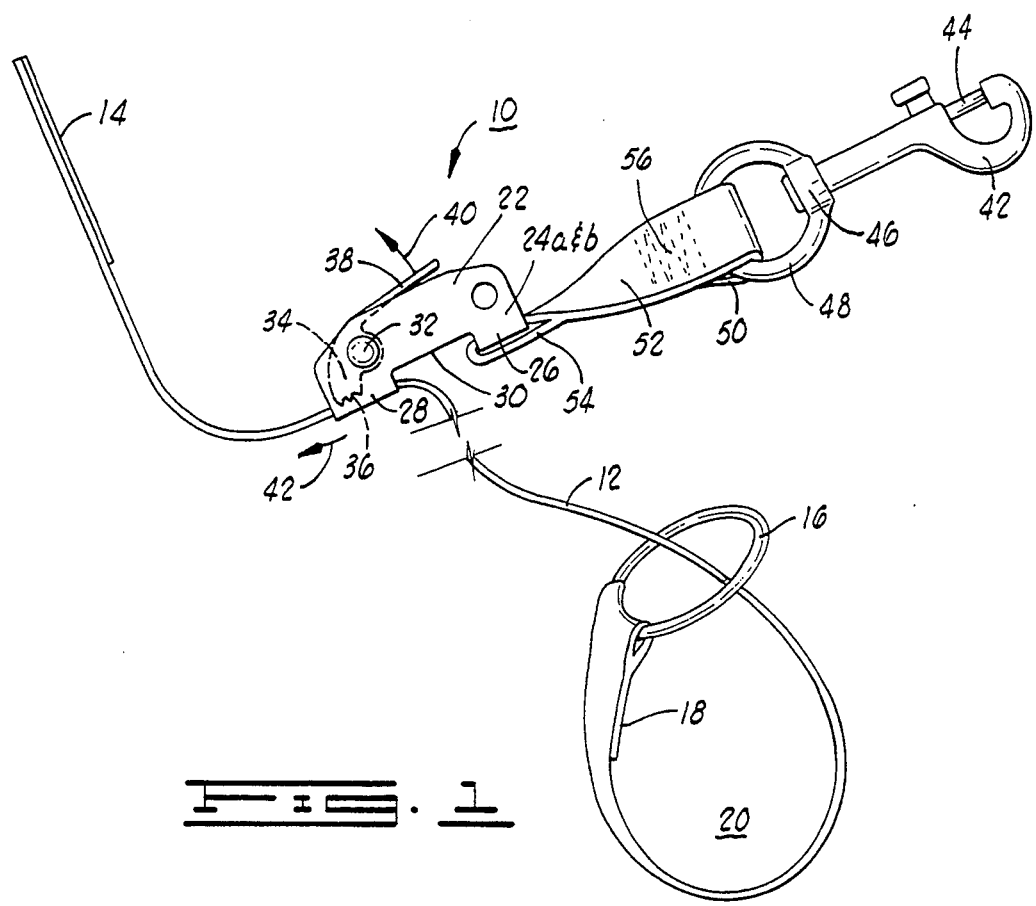
FIG. 1 is a perspective view of the restraining device of the present invention.

Referring to FIG. 1, the restraining device 10 consists of an elongate control strap 12 having a handle end 14 and a metal ring 16 extending from the opposite end as it is secured by the stitched flap or loop 18 of strap 12. The control strap 12 is passed through ring 16 in order to form a loop 20 while the remainder of control strap 12 is passed through a quick-release adjustable slide clamp in the form of a cam buckle 22. The control strap 12 may be a selected length, e.g., 81 inches, of one-inch wide nylon webbing.

The cam buckle 22 is a commercially available fixture of well-known type which is sold under the trademark ANCRA ™ and consists of a metal frame comprised of a bent formation of opposite side frames 24a and b which are bent parallel on opposite sides of bridges 26 and 28 leaving a center clearance 30 for receiving the control strap 12. A retaining pin 32 is secured across between side walls 24a and b and a spring-urged cam 34 having toothed surface 36 and control lever 38 is rotatably secured thereon. The cam 34 is normally spring-urged in the direction of arrow 40 to retain the control strap 12 in a locked position resisting movement of control strap 12 except in the direction of arrow 42. Thus, after initial setting of the position of cam buckle 22, the control strap 12 is free for manual movement in the direction of arrow 42 and cannot be moved in the opposite direction. However, to lengthen the control strap 12, i.e., increase the distance between loop 20 and cam buckle 22, one need only press down on cam lever 38 (opposite to arrow 40) to release the toothed engagement of teeth 36 in control strap 12.

A snap hook 42 having spring-loaded latch dog 44 is connected via a swivel base 46 into a metal ring 48. The hook ring 48 is connected through a loop 50 of a connector strap 52 which is connected at the other end via a strap loop 54 to the bridge 26 of cam buckle 22. The control strap 52 may be constructed from a short length of one-inch wide nylon webbing which is folded over to form the respective loops 50 and 54 as cross-stitching 56 secures the finished strap 52. The control strap 52 has a length of about five inches from end-to-end.

OPERATION

There is a recognized need among law enforcement officers for an effective means of physical control of drunken and/or aggressive prisoners. It is not unusual for squad cars, police stations and appurtenant structures to be damaged by prisoners who commit mayhem by kicking and otherwise damaging the surrounds. This is an expensive proposition from a repair standpoint, and quite often peace keeping officers may sustain serious injuries while subduing prisoners during transportation uprisings. The present invention fulfills many valuable functions which were not heretofore available for prisoner surveillance and control.

Figure 2:
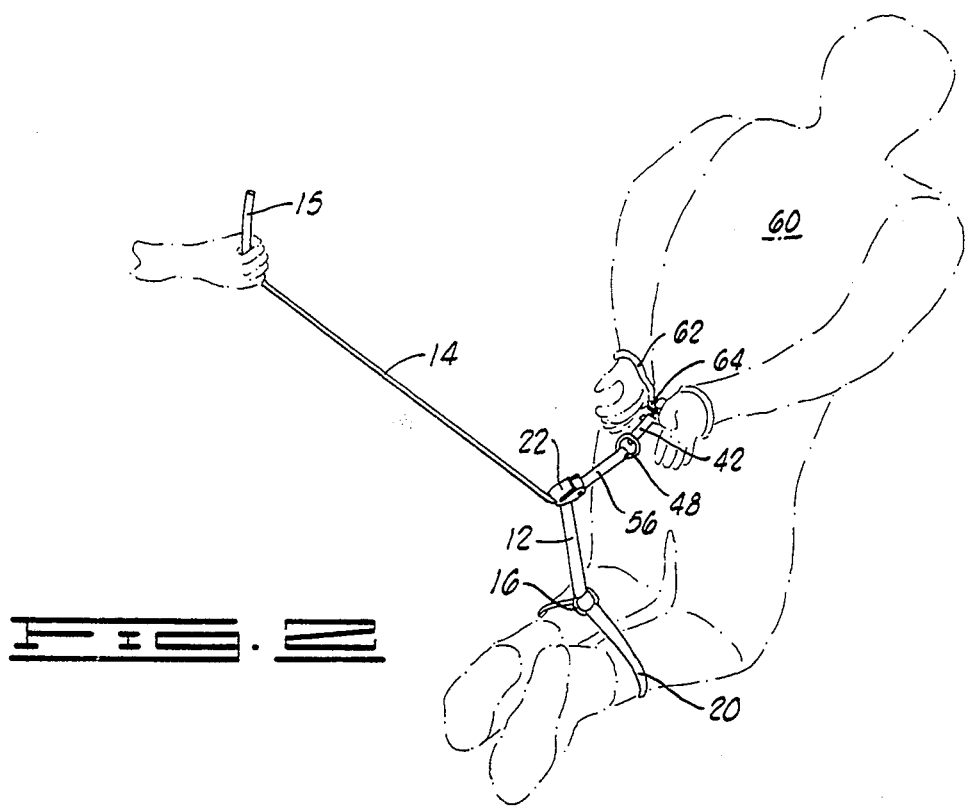
FIG. 2 is a view in perspective of the restraining device in operation.

As shown in FIG. 2, the prisoner 60 is shown in the kneeling position with wrists restrained behind him by means of handcuffs 62. In attending a prisoner 60, he is first handcuffed by means of the conventional bracelet handcuffs 62 having a flexible center link 64 interconnecting the left and right bracelets of the cuffs. The attending officer can then place the snap hook 42 onto the center link 64 of handcuffs 62 while then placing the loop 20 around the prisoner's ankles. The control strap 14 is led through the opening 30 (FIG. 1) of cam buckle 22 and beneath the cam lever 34 leaving the grip or handle end 14 of strap 12 to be attended by the arresting authority. If the prisoner is relatively calm, the cam buckle 22 may be set to provide a longer length of strap 12 and strap 56 such that the prisoner 60 can sit comfortably in a squad car, squad room chair or the like. Should the prisoner 60 begin acting up or attempting to damage his surrounds, it is only necessary for the attending officer to pull on strap handle end 14 thereby pulling the strap 12 in the direction of arrow 42 (FIG. 1) to shorten the effective length between the ankle loop 20 and the snap hook 42 on the handcuff 62 of the prisoner 60. The greater the amount of shortening, i.e., tightening of the ankle/wrist connection, the greater is the degree of disablement to the prisoner 60.

Once a prisoner is delivered to a more central authority and there is a need to unshackle the prisoner, it is only necessary for the arrestor to depress the cam lever 38 (FIG. 1) by depressing in the direction opposite to arrow 40, thereby to release the grip of cam 34 and teeth 36 from gripping the control strap 12 such that the strap is free to release and slide in the reverse direction of arrow 42. As much slack as needed may be allowed in the length of control strap 12 and strap 56 to allow loosening of the loop 20 so that the prisoner can step out of the ankle binding for interrogation, incarceration or whatever.

The foregoing discloses a very effective restraining device for enabling whatever the required degree of control over a prisoner through arrest and transportation proceedings. The strap device includes enough adjustment to provide effective use on all sizes of prisoners whether small or large. Also, the restraining device is suitable for securing a prisoner's arms in those cases where it is required by excess weight that a prisoner must be handcuffed in front. In this case, the strap may be placed on the prisoner's upper arms and secured behind the back so that, when tightened, it tends to secure the prisoner's arms to his body.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A restraining device for use in combination with a prisoner hand binding, comprising:
    an elongate control strap forming a loop on one end for disposition around some portion of the prisoners's lower legs with the opposite end providing a hand grip;
    a releasable buckle means receiving the control strap opposite end therethrough to define a selected length of control strap between said control strap loop and said buckle means; and
    a connector strap with snap hook connecting the hand binding to said releasable buckle means;
    whereby hand grip control of said control strap enables immediate adjustment of the strap length between said hand binding and said loop.

2. A restraining device as set forth in claim 1 wherein said elongate control strap comprises:
    a selected length of nylon webbing having a metal ring on one end for forming said loop.

3. A restraining device as set forth in claim 1 wherein said releasable buckle means comprises:
    a cam buckle with spring urged cam holding the control strap in a selected position.

4. A restraining device as set forth in claim 2 wherein said releasable buckle means comprises:
    a cam buckle with spring urged cam holding the control strap in a selected position.

5. A restraining device as set forth in claim 1 wherein said strap with snap hook further comprises:
    a hook having a spring-loaded latch dog for connection to said hand binding.

6. A restraining device as set forth in claim 3 wherein said connector strap with snap hook further comprises:
    a hook having a spring-loaded latch dog for connection to said hand binding.

7. A restraining device as set forth in claim 3 wherein said cam buckle comprises:
    a channel-shaped frame receiving said control strap therethrough;
    a cam rotatively retained on said frame with gripping surface urged against said control strap; and
    a cam lever rigidly formed with said cam and depressible to release the cam gripping surface from against said control strap.

8. An article of manufacture for use on a person in handcuffs as a further physical restraint, comprising:
    an elongate control strap having a handle grip on one end and a metal ring secured to the other end for forming an adjustable loop;
    a cam buckle having a cam and grip releasing cam lever receiving said control strap therethrough for selective locking engagement by the cam; and
    a snap hook resiliently connected to said cam buckle, said snap hook serving to affix to said handcuffs.

* * * * *